United States Patent
Sauer et al.

(10) Patent No.: US 7,853,308 B2
(45) Date of Patent: Dec. 14, 2010

(54) SYSTEM AND METHOD FOR PATIENT POSITIONING FOR RADIOTHERAPY IN THE PRESENCE OF RESPIRATORY MOTION

(75) Inventors: Frank Sauer, Princeton, NJ (US); Ali Khamene, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 686 days.

(21) Appl. No.: 11/056,318

(22) Filed: Feb. 11, 2005

(65) Prior Publication Data

US 2005/0180544 A1 Aug. 18, 2005

Related U.S. Application Data

(60) Provisional application No. 60/545,116, filed on Feb. 17, 2004.

(51) Int. Cl.
*A61B 5/05* (2006.01)
(52) U.S. Cl. .................. 600/425; 600/426; 600/427; 600/529; 600/534; 378/62; 378/65
(58) Field of Classification Search .......... 600/425–427, 600/529, 534; 378/62, 65
See application file for complete search history.

(56) References Cited

U.S. PATENT DOCUMENTS

| 6,501,981 B1 * | 12/2002 | Schweikard et al. | ......... 600/427 |
| 6,778,850 B1 * | 8/2004 | Adler et al. | ................. 600/427 |
| 2002/0151786 A1 * | 10/2002 | Shukla et al. | ................ 600/411 |
| 2004/0092815 A1 * | 5/2004 | Schweikard et al. | ........ 600/425 |

\* cited by examiner

*Primary Examiner*—Brian Casler
*Assistant Examiner*—John F Ramirez
(74) *Attorney, Agent, or Firm*—Donald B. Paschburg; F. Chau & Associates, LLC

(57) ABSTRACT

A system and method for positioning a patient for radiotherapy is provided. The method comprises: acquiring a first x-ray image sequence of a target inside the patient at a first angle; acquiring first respiratory signals of the patient while acquiring the first x-ray image sequence; acquiring a second x-ray image sequence of the target at a second angle; acquiring second respiratory signals of the patient while acquiring the second x-ray image sequence; synchronizing the first and second x-ray image sequences with the first and second respiratory signals to form synchronized first and second x-ray image sequences; identifying the target in the synchronized first and second x-ray image sequences; and determining three-dimensional (3D) positions of the target through time in the synchronized first and second x-ray image sequences.

27 Claims, 3 Drawing Sheets

SYSTEM AND METHOD FOR PATIENT POSITIONING FOR RADIOTHERAPY IN THE PRESENCE OF RESPIRATORY MOTION

CROSS-REFERENCE TO RELATED APPLICATION

This application claims the benefit of U.S. Provisional Application No. 60/545,116, filed Feb. 17, 2004, the disclosure of which is incorporated by reference herein in its entirety.

BACKGROUND OF THE INVENTION

1. Technical Field

The present invention relates to patient positioning for radiotherapy, and more particularly, to a system and method for patient positioning for radiotherapy in the presence of respiratory motion.

2. Discussion of the Related Art

Radiation treatment or radiotherapy involves the treatment of a disease with radiation, especially by selective irradiation with x-rays or other ionizing radiation and by ingestion of radioisotopes. During radiation treatment, high-energy x-rays or electron beams are generated by a linear accelerator (LINAC) and directed towards a cancerous target anatomy. The goal of the treatment is to destroy the cancerous cells within the target anatomy without causing undue side effects that may result from harming surrounding healthy tissue and vital organs during treatment.

Radiation treatment typically takes place over the course of several sessions during which a delivered radiation dose is broken into several portal fields. For each field, a LINAC gantry is rotated to different angular positions, spreading out the dose delivered to healthy tissue. At the same time, the beam remains pointed towards the target anatomy, which had been placed in the isocenter of the beam by positioning the patient.

Patient positioning is typically achieved by placing a set of tattoos on the patient's skin and aligning the tattoos with a pair of lasers. This is accomplished by imaging the cancerous area of the patient with a computed tomography (CT) scanner and tattooing marks on the patient's skin corresponding to the location of the cancerous area in conjunction with the alignment lasers. The alignment lasers are included in a treatment room with the CT scanner, and the patient is aligned with the lasers while the patient is on a table so that the patient's tattoos line up with the lasers. In this way, a coordinate system of a CT treatment plan can be registered with the coordinate system of a LINAC for delivery of the radiation dose.

The skin marking system, however, has limited accuracy. For example, the skin markers are not rigidly connected to the target anatomy. Thus, a shift can easily occur between the external markers and internal target anatomy due to weight loss of the patient, thereby resulting in an imprecise delivery of the radiation dose. In order to overcome this, image guided radiation therapy (IGRT) has been introduced. IGRT employs medical imaging modalities such as x-ray, ultrasound, CT, or magnetic resonance imaging (MRI) in conjunction with a LINAC gantry for patient positioning.

When using IGRT with the above-mentioned modalities, the principle of patient positioning is mostly the same. For example, the acquired images show the current location of the internal target anatomy. The images are registered with the LINAC coordinate system, which is independent of the position of the patient table, thereby allowing the table and the patient to be moved into a position that aligns the target anatomy with the isocenter of the LINAC gantry.

Another modality for use with IGRT is portal imaging. In portal imaging, the LINAC directly acquires images with the same beam used for treatment. Portal imaging is based on combining film based portal imaging with computer image processing and registration techniques to yield patient positioning data. This modality has been particularly advantageous because one does not have to register a "set-up modality" with a "treatment modality". Portal imaging does, however, have a few limitations in that soft tissue is more or less transparent to the LINAC's high-energy beam and portal images show only bone structures.

Although IGRT reduces the drawbacks associated with correlating external markers with internal targets, IGRT techniques consider the body as a rigid object during dose delivery. Thus, because the patient is breathing during treatment, the target anatomy may move several centimeters due to the patient's respiration. In order to take into account respiratory motion during radiation treatment, several suggestions have been made. One suggestion has been to a gate the treatment beam. In other words, to switch the treatment beam on or off with respect to the patient's respiratory motion. Another has been to track the target by moving the beam along the target using collimator leaves in a multileaf collimator, and yet another has been to adapt the treatment plan's dose distribution to the target's spatiotemporal distribution.

Some of these techniques have been proposed to be implemented with four-dimensional (4D) CT scanners. This, however, has proven to be undesirable as the cost of placing a 4D CT scanner in every treatment room is high and because pre-treatment 4D CT data may not necessarily give correct information regarding the patient's respiratory motion. In another technique, fluoro x-ray images have been taken at the same angle as that of a planned treatment field, thus enabling observation of target movement in the time sequence of two-dimensional (2D) projection images. However, for each field during a treatment session, the projected 2D target has to be re-determined requiring that the patient be moved between an x-ray treatment simulator and the LINAC.

In yet another technique, radiosurgery can be performed using a modified cyberknife. Radiosurgery with a cyberknife is a one-time procedure that uses a lightweight LINAC mounted to a robotic arm having six degrees of freedom. Two x-ray systems are mounted on the ceiling and floor of a treatment room and are used in conjunction with an optical tracking system and optical markers attached to a patient to track the position of the target during respiratory motion. The ongoing x-ray imaging of this technique is not appropriate for radiotherapy, as radiotherapy takes place over many treatment sessions and because it uses excess radiation. Moreover, the inclusion of two x-ray systems in a treatment room is a costly proposition.

Accordingly, there is a need for a technique of locating and tracking cancerous target anatomies in the presence of respiratory motion that reduces radiation exposure to nearby healthy tissue in a cost-effective manner.

SUMMARY OF THE INVENTION

The present invention overcomes the foregoing and other problems encountered in the known teachings by providing a system and method for patient positioning for radiotherapy in the presence of respiratory motion.

In one embodiment of the present invention, a method for positioning a patient for radiotherapy, comprises: acquiring a first x-ray image sequence of a target inside the patient at a first angle; acquiring first respiratory signals of the patient while acquiring the first x-ray image sequence; acquiring a second x-ray image sequence of the target at a second angle; acquiring second respiratory signals of the patient while acquiring the second x-ray image sequence; synchronizing the first and second x-ray image sequences with the first and second respiratory signals to form synchronized first and second x-ray image sequences; identifying the target in the synchronized first and second x-ray image sequences; and determining three-dimensional (3D) positions of the target through time in the synchronized first and second x-ray image sequences.

The first and second x-ray image sequences are two-dimensional (2D) image sequences. The first angle is 0 degrees and the second angle is 90 degrees. The step of synchronizing the first and second x-ray image sequences comprises resolving a time delay between the first and second respiratory signals. The synchronized first and second x-ray image sequences represent the first and second x-ray image sequences if they were acquired at the same time.

The step of identifying the target in the synchronized first and second x-ray image sequences comprises selecting the target from one image of the synchronized first and second x-ray image sequences and tracking the target in the remaining images of the synchronized first and second x-ray image sequences. The step of determining the 3D position of the target through time comprises extracting the target from the synchronized first and second x-ray image sequences and performing a triangulation using the first and second angles.

The method further comprises matching the 3D positions of the target from the synchronized first and second x-ray image sequences with four-dimensional (4D) positions of the target acquired from a computed tomography (CT) scan of the patient and generating a graphical user interface (GUI) having a first window for displaying the 3D positions of the target that match the 4D positions of the target. The GUI includes a second window for displaying a metric representing a difference between the 3D positions of the target and the 4D positions of the target.

The method further comprises: generating a first x-ray image sequence of the 3D positions of the target and a first digitally reconstructed radiograph (DRR) illustrating the 4D positions of the target; overlaying the first x-ray image sequence of the 3D positions of the target and the first DRR to determine one of matching and non-matching 3D positions of the target and 4D positions of the target; positioning the patient and performing radiotherapy in accordance with the matched 3D and 4D positions of the target; and tracking internal markers while acquiring the first and second x-ray image sequences. The data associated with the internal markers is used to determine the 3D positions of the target with a triangulation method.

In another exemplary embodiment of the present invention, a system for positioning a patient for radiotherapy, comprises: a memory device for storing a program; a processor in communication with the memory device, the processor operative with the program to: acquire a first x-ray image sequence of a target inside the patient at a first angle; acquire first respiratory signals of the patient while acquiring the first x-ray image sequence; acquire a second x-ray image sequence of the target at a second angle; acquire second respiratory signals of the patient while acquiring the second x-ray image sequence; synchronize the first and second x-ray image sequences with the first and second respiratory signals to form synchronized first and second x-ray image sequences; identify the target in the synchronized first and second x-ray image sequences; and determine 3D positions of the target through time in the synchronized first and second x-ray image sequences.

The first and second x-ray image sequences are acquired using an x-ray machine. The x-ray machine is mounted on a linear accelerator (LINAC) device. The x-ray machine acquires the first and second x-ray image sequences using one of a kilo-electron volt (KeV) and mega-electron volt (MeV) beam. The first and second respiratory signals are acquired using one of a respiratory monitoring belt and an optical tracking device.

The processor is further operative with the program code to match the 3D positions of the target from the synchronized first and second x-ray image sequences with 4D positions of the target acquired from a CT scan of the patient. The CT data is acquired by using one of a CT, helical CT, positron emission tomographic (PET), fluoroscopic, ultrasound and magnetic resonance (MR) imaging device.

The processor is further operative with the program code to track internal markers while acquiring the first and second x-ray image sequences. The internal markers are gold balls. The processor is further operative with the program code to perform radiotherapy in accordance with the matched 3D and 4D positions of the target.

In yet another exemplary embodiment of the present invention, a method for positioning a patient for image guided radiation therapy (IGRT), comprises: acquiring image data associated with a cancerous target inside the patient using a CT imaging technique; acquiring a first x-ray image sequence of the target at a first angle and first respiratory signals of the patient; acquiring a second x-ray image sequence of the target at a second angle and second respiratory signals of the patient; synchronizing the first and second x-ray image sequences with the first and second respiratory signals to form synchronized first and second x-ray image sequences; selecting the target from one image of the synchronized first and second x-ray image sequences and tracking the target in the remaining images of the synchronized first and second x-ray image sequences; and extracting the target from the synchronized first and second x-ray image sequences and performing a triangulation using the first and second angles to determine 3D positions of the target through time in the synchronized first and second x-ray image sequences.

The first angle and the second angle are orthogonal to each other. The method further comprises matching the 3D positions of the target from the synchronized first and second x-ray image sequences with 4D positions of the target acquired from a CT scan of the patient and positioning the patient and performing the IGRT in accordance with the matched 3D and 4D positions of the target.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Figure 1:
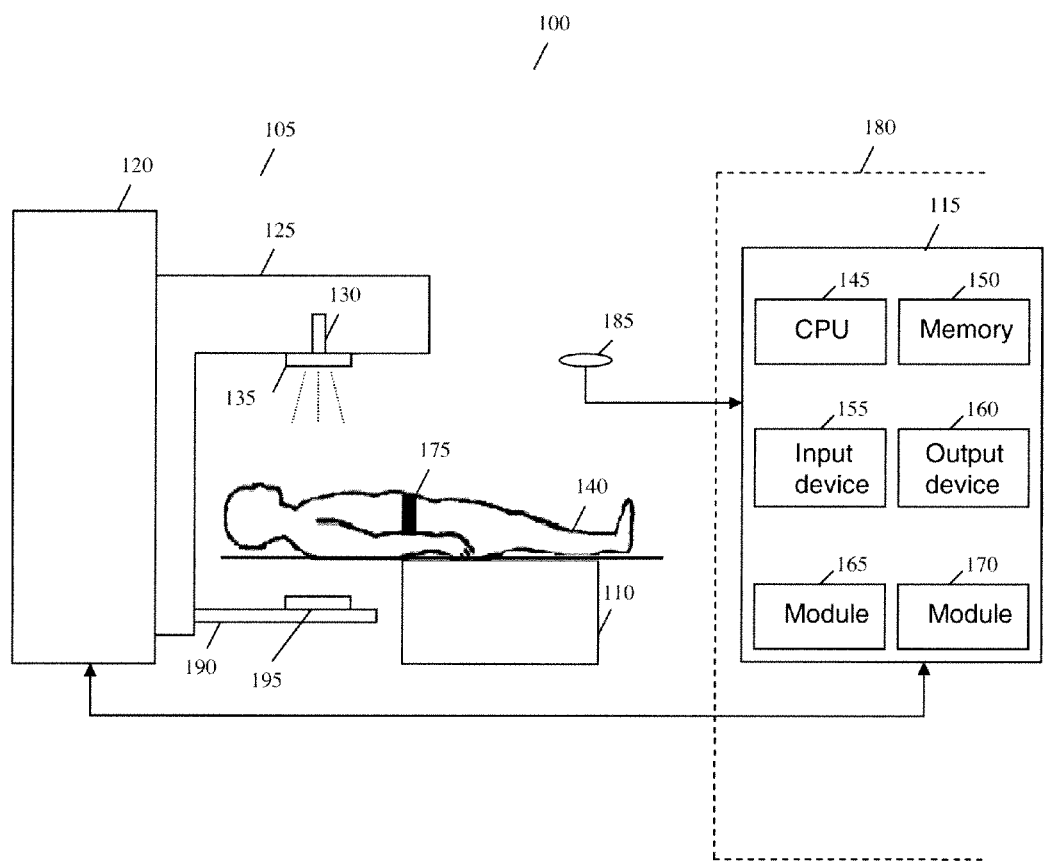
FIG. 1 is a block diagram of a system for patient positioning for radiotherapy according to an exemplary embodiment of the present invention.

FIG. 1 is a block diagram of a system 100 for patient positioning for radiotherapy in view of respiratory motion according to an exemplary embodiment of the present invention. As shown in FIG. 1, the system 100 includes a linear accelerator (LINAC) device 105, a bed 110 and a treatment unit 115. The LINAC device 105 includes, inter alia, a base 120, which includes a control unit for controlling the LINAC device 105, and a gantry 125. The gantry 125 includes a LINAC 130 or an x-ray kilo-electron volt (KeV) imaging source, a beam-shielding device (not shown) within a treatment head 135, and a KeV or mega-electron volt (MeV) imaging panel 195 attached to an electronic portal imaging device 190.

The gantry 125 can be swiveled about a horizontal axis during the course of radiation treatment or radiotherapy. The treatment head 135 is fixed to the gantry 125 for movement therewith, and the LINAC 130 or x-ray KeV imaging source generates high-powered radiation such as electron, photon or any other detectable radiation. The movement of the gantry 125 and distribution of radiation from the LINAC 130 are controlled by the control unit in response to commands issued from the treatment unit 115. The treatment unit 115 is located either in a room separate from where the LINAC device 105 is located or in a shielded area 180 of a room where the LINAC device 105 is located.

As shown in FIG. 1, the electronic portal imaging device 190 is mounted to the gantry 125. Portal images can be obtained at any gantry 125 angle and during rotation of the gantry 125. The portal imaging device 190 includes the imaging panel 195, which may be a flat panel amorphous silicon detector implemented as one or more arrays of photo-sensors. The panel 195 is capable of measuring the radiation exiting the patient 140. The amount of radiation exiting the patient 140 can be used to gather the patient's 140 exit dose information. The delivered radiation dose can then be compared to a planned delivery dose using digitally reconstructed radiographs (DRRs) generated by the treatment unit 115 to determine if the delivered radiation dose went as planned.

The treatment unit 115 includes, inter alia, a central processing unit (CPU) 145 and a memory 150, both of which may be connected to an input device 155 and output device 160. The treatment unit 115 includes a module 165 that includes one or more methods for positioning a patient for radiotherapy in view of respiratory motion. The treatment unit 115 also includes a module 170 that includes patient treatment information based on previously acquired computed tomography (CT) data. The memory 150 may include a random access memory (RAM) and a read only memory (ROM). The memory 150 may also include a database, disk drive, tape drive, or a combination thereof for storing patient treatment information. The input 155 may be constituted by a keyboard or mouse and the output 160 may be constituted by a liquid crystal display (LCD) or cathode ray tube (CRT) display.

As further shown in FIG. 1, a patient 140 includes a respiratory monitor 175 in the form of a belt secured to a portion of his chest. The respiratory monitor 175 may be, for example, a respiratory monitoring belt such as a strain gauge that generates a signal in synch with the breathing motion of the patient's 140 chest. The signal may be transmitted to the treatment unit 115 via a senor 185 or directly via a hardwired connection. The respiratory monitor 175 may also be an optical marker attached to the patient's chest or abdomen that works in conjunction with the sensor 185, which in this example is an optical sensor, to transmit data associated with the respiratory state of the patient 140 to the treatment unit 115.

Figure 2:
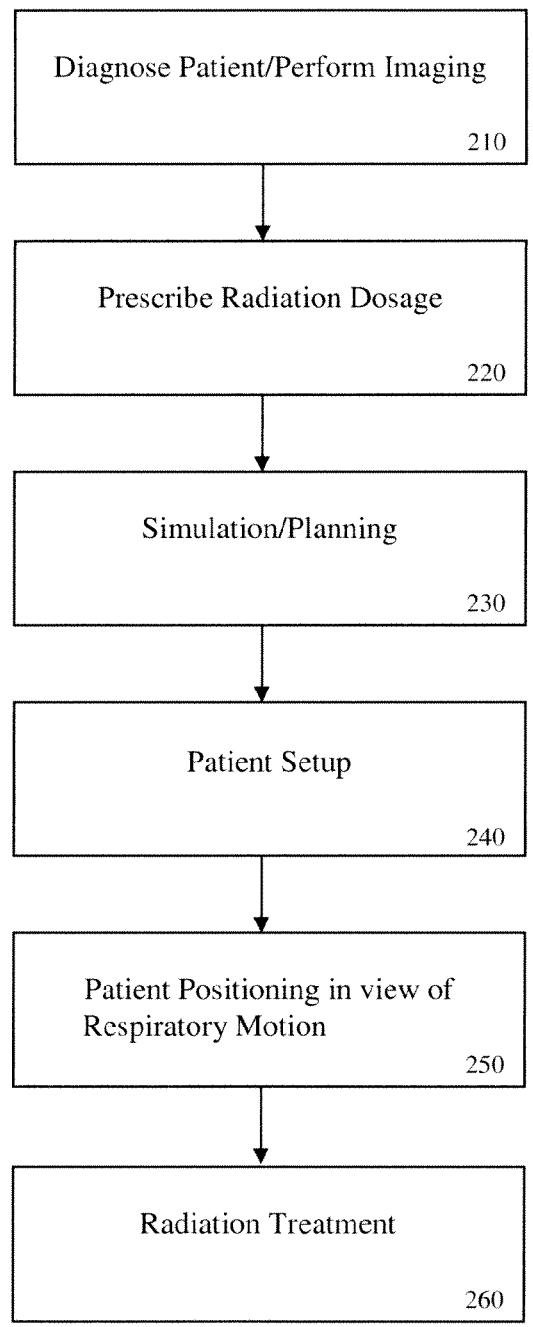
FIG. 2 is a flowchart illustrating a method of image guided radiation treatment (IGRT) employing a method for patient positioning for radiotherapy according to an exemplary embodiment of the present invention.

FIG. 2 is a flowchart illustrating a method of image guided radiation treatment (IGRT) employing a method for patient positioning for radiotherapy in view of Respiratory motion according to an exemplary embodiment of the present invention. As shown in FIG. 2, a patient 140 who has gone to a medical practitioner, such as an oncologist, undergoes diagnosis for a cancer (210). In this example, the patient 140 is diagnosed with a cancerous tumor. Once the patient 140 is diagnosed, a CT scan of the cancerous area is performed under the direction of the medical practitioner. The resulting CT scan generates multiple x-ray images of the patient 140 and assimilates the images into two-dimensional (2D) cross-sectional images of the patient's 140 body for analysis.

Data from the CT scan may then be used by the medical practitioner to prescribe medication (220) and to further diagnose the cancerous tumor. For example, the CT data may be used to delineate diseased tissue and healthy organs at risk, to define a treatment isocenter and to configure certain properties of a radiation beam to be applied to the patient 140. After the patient 140 has been prescribed with medication to treat the tumor, a virtual simulation of the treatment may take place (230).

In this step, a graphic simulation of the treatment process is performed. This gives the medical practitioner the flexibility needed to treat the tumor while avoiding healthy tissue or organs that may be at risk. Next, the patient 140 is prepared for radiation treatment (240). This is accomplished, for example, by placing marks using a laser projector on the patient's 140 skin that are associated with the cancerous tumor. The marks will be used to position the patient 140 under the LINAC device 105. After the patient 140 has been marked, he is transported to a room for radiation treatment and then positioned under a LINAC device 105.

Figure 3:
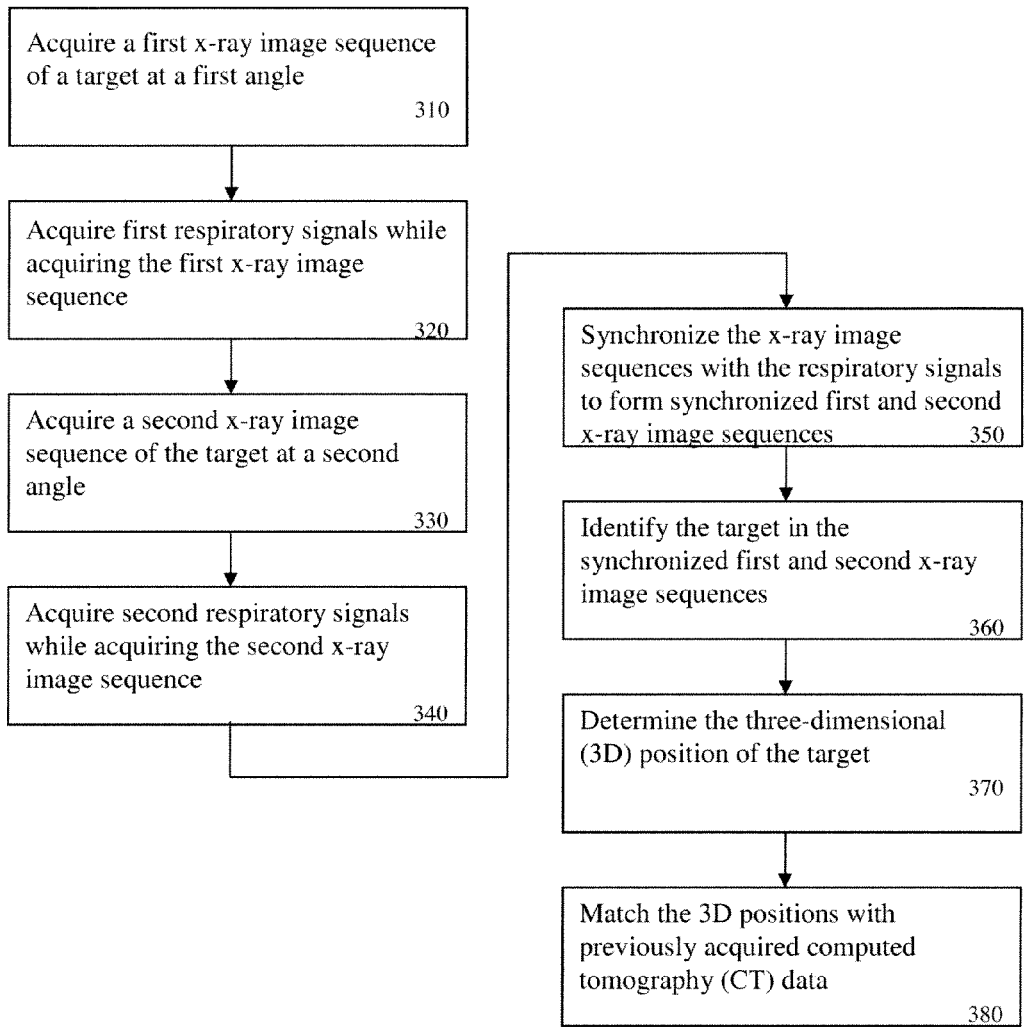
FIG. 3 is a flowchart illustrating the method for patient positioning for radiotherapy according to an exemplary embodiment of the present invention.

Prior to performing radiation treatment, the patient 140 is positioned under the LINAC device 105 in accordance with an exemplary embodiment of the present invention (250). This is accomplished, by first positioning the patient 140 so that the center of an area to be radiated (e.g., the target anatomy) or the patient's 140 isocenter is located at the LINAC's 130 isocenter by orienting the gantry 125. Next, as shown in FIG. 3, a high-powered radiation beam is projected from the LINAC 130 and a 2D x-ray image sequence of the target is acquired (310). The x-ray image sequence is acquired from a first angle of the gantry 125. During this time, respiratory signals indicative of the patient's 140 breathing pattern are captured by the respiratory monitor 175 and transmitted to the treatment unit 115 (320).

After acquiring the first x-ray image sequence and its accompanying respiratory signals at the first gantry 125 angle, the gantry 125 is moved to another angle, which is orthogonal to the first angle, and another 2D x-ray image sequence is acquired (330). Simultaneous to the acquisition of the second x-ray image sequence, respiratory signals are captured by the respiratory monitor 175 and transmitted to the treatment unit 115 (340). At the treatment unit 115, the x-ray image sequences and their associated respiratory signals are synchronized (350). The x-ray sequences and respiratory signals can be synchronized because the x-ray sequences are captured using an external trigger signal having a fixed frequency and the respiratory monitor 175 is digitized using the same trigger signal. Thus, the frames of the x-ray sequences and samples of the respiratory signals are numbered with count increments of the external trigger signal.

Therefore, the x-ray sequences and respiratory signals can be retrospectively synchronized if the inherent time delay for capturing an x-ray image is known. Thus, by resolving a time delay associated with the respiratory signals, the x-ray image sequences and their associated respiratory signals are synchronized. It is to be understood, however, that the process of resolving the time delay is simplified as the profile of the respiratory signals is expected to remain consistent due to the shortness of their acquisition period. After resolving the time delay, two synchronized x-ray image sequences are created that represent the first and second x-ray image sequences if they were simultaneously acquired at the first and second gantry 125 angles.

Upon synchronization, the target may then be identified and tracked through each synchronized x-ray image sequence (360). This is accomplished, for example, by the medical practitioner identifying the target on the output device 160 of the treatment unit 115. By using a mouse or a stylus pen, the medical practitioner may then draw a bounding box around the target and using an image processing technique the target may be tracked throughout each synchronized x-ray image sequence. An image processing technique such as, finding the maximum cross-correlation coefficient between the selected region and the images within the x-ray image sequence while imposing temporal consistency using Kalman filtering may be used.

Subsequently, the target may be extracted from each synchronized x-ray image sequence and a three-dimensional (3D) position of the target can be determined (370). This is accomplished by performing a triangulation using the first and second angles. The triangulation of the first and second angles yields the 3D position of the target by utilizing the geometry of the x-ray beam and the image plane of the LINAC device 105, which would have been previously acquired during calibration of the LINAC device 105. The triangulation procedure may also take into account any uncertainties associated with locating the target in the x-ray image sequences by reflecting the uncertainties as an uncertainty measure for the extracted target.

Once the 3D positions of the target have been determined, they are compared with corresponding CT data to see if they match (380). This occurs by using either the extracted data for the target and a previously planned four-dimensional (4D) trajectory of the target from the CT scan or by providing a metric indicating a difference in the two trajectories. If the 3D positions and CT data match, the patient 140 is positioned according to the target position information derived therefrom and a simulated radiation treatment scenario proceeds unchanged (260). In other words, beam gating or tracking is performed according to the position information derived from the matched 3D position and CT data, thereby enabling the radiation dose to be properly delivered during the treatment session from different angles. It is to be understood, however, that if there is a significant change in the planned treatment, the plan should not be used, and the plan should be adjusted using a newly acquired trajectory of the tumor before performing radiation treatment.

Thus, in accordance with an exemplary embodiment of the present invention, a single x-ray system may be employed to acquire two x-ray image sequences of a patient from different angles. The x-ray image sequences are acquired one after the other and are retrospectively synchronized with corresponding respiratory monitoring signals of the patient. Using the synchronized data, the 3D trajectory of a target anatomy with respect to the respiratory monitoring signals can be determined. Once the 3D trajectory of the target has been determined, patient set-up is performed according to IGRT and the patient is positioned according to the 3D trajectory of the target. Radiation treatment may then be performed with beam tracking and/or gating using the 3D trajectory of the target, thus allowing for motion compensation for all fields in which radiation doses are being delivered during the treatment session and from different angles. Therefore, radiation treatment may be dynamically adapted to track organ motion during a treatment session, enabling accurate delivery of the radiation dose and minimizing the exposure of surrounding tissue.

In an alternative embodiment of the present invention, an x-ray system or source may be mounted on a C-arm separate from LINAC gantry. The C-arm may be, for example, a remotely controlled robotic arm. In another alternative embodiment of the present invention, a biplane x-ray system may be used to acquire the two x-ray image sequences. In yet another alternative embodiment of the present invention, a portal imaging technique may be used to measure the respiratory motion of the patient.

In another alternative embodiment of the present invention, the angles at which the x-ray image sequences are acquired may be 0 degrees and 90 degrees. In yet another alternative embodiment, the angles may be closer than 90 degrees apart when performing radiation treatment in only two fields.

In an alternative variant of the present invention, a graphical user interface (GUI) having a window for displaying the 3D positions of the target that match the 4D positions of the target may be generated and displayed on a computer display at the treatment unit. The GUI may further be configured to include another window for displaying a metric representing a difference between the 3D positions of the target and the 4D positions of the target.

In yet another variant of the present invention, internal markers may be introduced into a patient prior to performing a CT scan. For example, the internal markers, which may be gold balls a few millimeters in diameter, may be implanted near the target. As they will be implanted prior to the CT scan, their location with respect to the target will be known from the CT data. Moreover, as the markers show up having a high contrast in x-ray images, they will aid in locating the target.

It is to be further understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for positioning a patient for radiotherapy, comprising:
   acquiring a first x-ray image sequence of a target inside the patient by projecting a radiation beam from a linear accelerator positioned at a first angle;
   acquiring first respiratory signals of the patient while acquiring the first x-ray image sequence;
   acquiring a second x-ray image sequence of the target by projecting a radiation beam from the linear accelerator positioned at a second angle;
   acquiring second respiratory signals of the patient while acquiring the second x-ray image sequence, wherein the second x-ray image sequence and second respiratory signals are acquired after the first x-ray image sequence and first respiratory signals;
   retrospectively synchronizing the first and second respiratory signals with each other to form synchronized first and second x-ray image sequences;
   identifying the target in the synchronized first and second x-ray image sequences; and
   determining three-dimensional (3D) positions of the target through time in the synchronized first and second x-ray image sequences.

2. The method of claim 1, wherein the first and second x-ray image sequences are two-dimensional (2D) image sequences.

3. The method of claim 1, wherein the first angle is 0 degrees and the second angle is 90 degrees.

4. The method of claim 1, wherein the step of synchronizing the first and second respiratory signals, comprises:
   resolving a time delay between the first and second respiratory signals.

5. The method of claim 1, wherein the synchronized first and second x-ray image sequences represent the first and second x-ray image sequences if they were acquired at the same time.

6. The method of claim 1, wherein the step of identifying the target in the synchronized first and second x-ray image sequences, comprises:
   selecting the target from one image of the synchronized first and second x-ray image sequences; and
   tracking the target in the remaining images of the synchronized first and second x-ray image sequences.

7. The method of claim 1, wherein the step of determining the 3D position of the target through time, comprises:
   extracting the target from the synchronized first and second x-ray image sequences; and
   performing a triangulation using the first and second angles.

8. The method of claim 1, further comprising:
   matching the 3D positions of the target from the synchronized first and second x-ray image sequences with four-dimensional (4D) positions of the target acquired from a computed tomography (CT) scan of the patient.

9. The method of claim 8, further comprising:
   generating a graphical user interface (GUI) having a first window for displaying the 3D positions of the target that match the 4D positions of the target.

10. The method of claim 9, wherein the GUI includes a second window for displaying a metric representing a difference between the 3D positions of the target and the 4D positions of the target.

11. The method of claim 8, further comprising:
    generating a first x-ray image sequence of the 3D positions of the target and a first digitally reconstructed radiograph (DRR) illustrating the 4D positions of the target.

12. The method of claim 11, further comprising:
    overlaying the first x-ray image sequence of the 3D positions of the target and the first DRR to determine one of matching and non-matching 3D positions of the target and 4D positions of the target.

13. The method of claim 8, further comprising:
    positioning the patient and performing radiotherapy in accordance with the matched 3D and 4D positions of the target.

14. The method of claim 1, further comprising:
    tracking internal markers while acquiring the first and second x-ray image sequences.

15. The method of claim 1, wherein the first and second x-ray image sequences are acquired using a trigger signal having a predetermined frequency and the first and second respiratory signals are digitized using the trigger signal.

16. A system for positioning a patient for radiotherapy, comprising:
    a memory device for storing a program,
    a processor in communication with the memory device, the processor operative with the program to:
    acquire a first x-ray image sequence of a target inside the patient by projecting a radiation beam from a linear accelerator positioned at a first angle;
    acquire first respiratory signals of the patient while acquiring the first x-ray image sequence;
    acquire a second x-ray image sequence of the target by projecting a radiation beam from the linear accelerator positioned at a second angle;
    acquire second respiratory signals of the patient while acquiring the second x-ray image sequence, wherein the second x-ray image sequence and second respiratory signals are acquired after the first x-ray image sequence and first respiratory signals;
    retrospectively synchronize the first and second respiratory signals with each other to form synchronized first and second x-ray image sequences;
    identify the target in the synchronized first and second x-ray image sequences; and
    determine three-dimensional (3D) positions of the target through time in the synchronized first and second x-ray image sequences.

17. The system of claim 16, wherein the radiation beams are kilo-electron volt (KeV) or mega-electron volt (MeV) beams.

18. The system of claim 16, wherein the first and second respiratory signals are acquired using one of a respiratory monitoring belt and an optical tracking device.

19. The system of claim 16, wherein the processor is further operative with the program to:
    match the 3D positions of the target from the synchronized first and second x-ray image sequences with four-dimensional (4D) positions of the target acquired from a computed tomography (CT) scan of the patient.

20. The system of claim 19, wherein the CT data is acquired by using one of a CT, helical CT, positron emission tomographic (PET), fluoroscopic, ultrasound and magnetic resonance (MR) imaging device.

21. The system of claim 16, wherein the processor is further operative with the program to:
track internal markers while acquiring the first and second x-ray image sequences.

22. The system of claim 21, wherein the internal markers are gold balls.

23. The system of claim 16, wherein the processor is further operative with the program to:
perform radiotherapy in accordance with the matched 3D and 4D positions of the target.

24. A method for positioning a patient for image guided radiation therapy (IGRT), comprising:
acquiring image data associated with a cancerous target inside the patient using a computed tomography (CT) imaging technique;
acquiring a first x-ray image sequence of the target by projecting a radiation beam from a linear accelerator positioned at a first angle and simultaneously acquiring first respiratory signals of the patient;
acquiring a second x-ray image sequence of the target by projecting a radiation beam from the linear accelerator positioned at a second angle and simultaneously acquiring second respiratory signals of the patient, wherein the second x-ray image sequence and second respiratory signals are acquired after the first x-ray image sequence and first respiratory signals;
synchronizing the first and second respiratory signals with each other after the first and second x-ray image sequences have been acquired to form synchronized first and second x-ray image sequences;
selecting the target from one image of the synchronized first and second x-ray image sequences and tracking the target in the remaining images of the synchronized first and second x-ray image sequences; and
extracting the target from the synchronized first and second x-ray image sequences and performing a triangulation using the first and second angles to determine 3D positions of the target through time in the synchronized first and second x-ray image sequences.

25. The method of claim 24, wherein the first angle and the second angle are orthogonal to each other.

26. The method of claim 24, further comprising:
matching the 3D positions of the target from the synchronized first and second x-ray image sequences with four-dimensional (4D) positions of the target acquired from a computed tomography (CT) scan of the patient.

27. The method of claim 26, further comprising:
positioning the patient and performing the IGRT in accordance with the matched 3D and 4D positions of the target.

* * * * *